United States Patent [19]

Simon

[11] Patent Number: 6,080,415
[45] Date of Patent: Jun. 27, 2000

[54] MAKE-UP PRODUCT COMBINING A PHOTOCHROMIC PIGMENT AND A UV SCREENING AGENT, AND USES THEREOF

[75] Inventor: Jean-Christophe Simon, Paris, France

[73] Assignee: L'Oreal, Paris, France

[21] Appl. No.: 09/339,097

[22] Filed: Jun. 24, 1999

[30] Foreign Application Priority Data

Jun. 25, 1998 [FR] France .................................. 98 08085

[51] Int. Cl.[7] .............................. A61K 7/00; A61K 7/42; A61K 7/44
[52] U.S. Cl. .............................. 424/401; 424/59; 424/60; 424/400
[58] Field of Search ................................ 424/59, 60, 400, 424/401

[56] References Cited

U.S. PATENT DOCUMENTS 5,730,961 3/1998 Goudjil ..................................... 424/61

FOREIGN PATENT DOCUMENTS 0 359 909 3/1990 European Pat. Off. .
0 526 712 2/1993 European Pat. Off. .
0 709 728 5/1996 European Pat. Off. .
0 847 751 6/1998 European Pat. Off. .

OTHER PUBLICATIONS

Kishino Shigeru, Patent Abstracts of Japan, vol. 5, No. 178 (C–078), Publication No. 56100709, Publication Date: Dec. 8, 1981.

Database WPI, Week 9549, Derwent Publications Ltd., London, GB, AN 95–380265, XP–002102228, "Photochromic complex for topical skin compsn.—comprises lamellar base and titanium oxide surface layer for excellent photochromic properties", JP 07–258580, Oct. 9, 1995.

Database WPI, Week 9735, Derwent Publications Ltd., London, GB, AN 97–381408, XP–002102229, "Glossy pigment for photochromic baseplate—prepared by baking mixture of mica, titanium oxide and one or more metals or metal compounds", JP 09–165532, Jun. 24, 1997.

Database WPI, Week 9542, Derwent Publications Ltd., London, GB, AN 95–325371, XP–002102248, Photochromic composite for topical compsn.—has titania layer on surface of thin plate like base material, of specified conditional parameters.

*Primary Examiner*—Shelley A. Dodson
*Attorney, Agent, or Firm*—Oblon, Spivak, McClelland, Maier & Neustadt, P.C.

[57] ABSTRACT

A cosmetic make-up product, comprising first and second components, separately packaged, each containing a cosmetically acceptable medium, the first component containing at least one photochromic coloring agent which is capable of producing at least one color in the presence of ultraviolet light, and the second component containing at least one agent which screens ultraviolet light.

31 Claims, No Drawings

MAKE-UP PRODUCT COMBINING A PHOTOCHROMIC PIGMENT AND A UV SCREENING AGENT, AND USES THEREOF

BACKGROUND OF THE INVENTION

1. Field of the Invention

The present invention relates to a cosmetic product intended for a new type of make-up, combining a photochromic coloring agent and an agent for screening ultraviolet (UV) light. This product comprises two cosmetic make-up compositions which can be applied successively to the skin, either of the human face or body, to the lips and to superficial body growths such as the nails, the eyelashes, the eyebrows or the hair. The invention also relates to a two-coat make-up process.

2. Description of the Background

Known make-up compositions consist of a suitable vehicle and of various coloring agents which are intended to give a certain color to the compositions, before and/or after they are applied to the skin, the lips or superficial body growths.

The range of coloring agents currently used by cosmeticians is fairly limited; these agents are mainly organic pigments, lakes, inorganic pigments or pearlescent pigments. Lakes give vivid colors, but most are unstable to light, to temperature and to pH. Some of them also have the drawback of causing unsightly marks on the skin after they have been applied, because of running of the dye. By contrast, inorganic pigments, in particular inorganic oxides, are very stable, but give rather dull, pale colors. Pearlescent pigments give varied, but never intense, colors with iridescent, but usually fairly weak effects. Moreover, certain conventional make-up products allow decorative effects to be created with colored patterns such as drawings, chessboard patterns, letters and the like. However, these patterns are visible regardless of the nature of the light, which makes the make-up "static".

Since make-up manufacturers and consumers are ever-increasingly in search of special effects and original colors, research continues for the discovery of new and useful colorants for cosmetic formulations.

SUMMARY OF THE INVENTION

Accordingly, one object of the present invention is to provide a cosmetic formulation which exhibits an improved colorant effect.

Briefly, this object and other objects of the present invention as hereinafter will become more readily apparent can be attained by a cosmetic make-up product, comprising first and second components, separately packaged, each containing a cosmetically acceptable medium, the first component containing at least one photochromic coloring agent which is capable of producing at least one color in the presence of ultraviolet light, and the second component containing at least one agent which screens ultraviolet light.

DETAILED DESCRIPTION OF THE PREFERRED EMBODIMENTS

The discovery of the invention is based on a new type of make-up which contains photochromic agents. By using a two-layer product whose undercoat contains at least one photochromic coloring agent, it has now been found, surprisingly, that it is possible to trace or draw patterns on such a coat (letters, drawings, chessboard patterns, etc.), in particular with a pencil or fine brush, and that, depending on the nature of the light, the patterns appear or disappear. The invention gives rise to a unique "play" make-up effect: the colored or uncolored patterns appear and disappear according to the light falling on the person wearing the make-up, like "invisible ink". The make-up thus appears to be "alive".

A photochromic coloring agent is an agent which has the property of changing color when it is exposed to ultraviolet light and of regaining its initial color when it is no longer exposed to such light, or else of changing from an uncolored state to a colored state, and vice-versa. In particular, this agent displays different colors depending on whether it is exposed to natural light or artificial light.

More specifically, a subject of the invention is a cosmetic make-up product comprising first and second components containing a cosmetically acceptable medium, which are packaged separately, the first component containing at least one photochromic coloring agent capable of producing at least one color in the presence of ultraviolet light, and the second component containing at least one agent for screening out ultraviolet light.

Each composition can be a loose or compacted powder, a foundation, a face powder, an eyeshadow, a concealer product, a blusher, a lipstick, a lip pencil, an eye pencil, a nail varnish or a make-up product for the body.

An aspect of the invention is also a make-up process for human skin, lips and/or superficial body growths, which consists of applying a first coat of a first component comprising a cosmetically acceptable medium and at least one photochromic coloring agent which is capable of producing at least one color in the presence of ultraviolet light to the skin, the lips and/or superficial body growths, and then of applying a second coat of a second component comprising a cosmetically acceptable medium and at least one agent for screening ultraviolet light, over a portion of the first coat.

The make-up product is, in particular, a make-up kit in which these two components are packaged in separate compartments or containers and are accompanied by suitable means of application.

The two-coat architecture of the invention can be adapted for any type of make-up product for human skin, either of the face, the scalp or the body, mucous membranes such as the lips and the insides of the lower eyelids, and superficial body growths such as the nails, the eyelashes, the hair, the eyebrows and even body hairs. The second coat which forms patterns can be applied with a pen, pencil or any other instrument such as a sponge, finger, fine brush, brush, feather, or the like. This two-coat architecture can also be applied to make-up accessories such as false nails, false eyelashes, wigs or adhesive pellets or patches on the skin or the lips such as stickers.

The invention also relates to a made-up support comprising a first coat of a first component comprising at least one photochromic coloring agent and a second coat of a second component partly applied onto the first coat and comprising at least one agent for screening ultraviolet light.

The first coat, which forms the basecoat, is also referred to as the photochromic coat, and the top coat is also referred to as the screening coat.

According to the invention, the second coat is applied onto only a part of the first coat. It can be applied either at one of the ends of the first coat or in the middle, or else discontinuously, in particular in the form of geometrical, symmetrical or asymmetrical patterns such as, for example, points, squares, circles, stars, alphanumeric inscriptions and any other figurative or non-figurative symbol, distributed in a random or ordered manner, with sharp or vague outlines.

Thus, the parts of the basecoat coated with patterns are protected from ultraviolet light and cannot be excited by the latter, in contrast to the exposed parts of the basecoat.

Depending on the nature of the photochromic coloring agent, and in the presence or absence of ultraviolet light, the patterns on the top coat will be seen on a colored background, which will be the color of the excited photochrome, or alternatively will disappear.

The photochromic coloring agents can be of any nature. When the photochromic composition is transparent in the absence of ultraviolet light and colored in the presence of ultraviolet light, the patterns do not appear when the made-up support is not exposed to ultraviolet light, for example, inside a residence, whereas they appear when the support is exposed to ultraviolet light, for example, in daylight outside residences or under ultraviolet lamps, because of a color difference between the background and the patterns. When the patterns appear, they in particular have the color of the support and in particular the color of the skin, the lips, the eyelashes, the nails or the hair, while the background is the color of the excited photochromic agent.

When the photochromic composition is colored in the absence of ultraviolet light and transparent in the presence of ultraviolet light, the patterns appear colored when the made-up support is not exposed to ultraviolet light, whereas they do not appear when the made-up support is exposed to ultraviolet light.

When the photochromic composition is colored such that there is a first color in the absence of ultraviolet light and a second color in the presence of ultraviolet light, the patterns (of the color of the support) appear on a colored background of the first color in the absence of ultraviolet light and they appear on a colored background of the second color in the presence of ultraviolet light.

In order to make the color patterns on a colored background appear in another color, it is possible to add to the composition containing the screening agent at least one monochromatic coloring agent such as those conventionally used in cosmetics.

An aspect of the invention is also the use of the above product to make patterns of color appear or disappear on human skin and/or lips and/or superficial body growths, depending on the presence or absence of ultraviolet light.

The first composition of the invention can comprise one or more photochromic coloring agents. Preferably, a single photochromic agent is used for ease of use and in order to reduce manufacturing costs. These photochromic agents can be pigments or dyes. The photochromic agents which can be used in the invention include, in particular, those described in DE 19643773, JP 08/0209119, JP 09/100469, JP 09/183969, JP 09/095670, JP 09/031453, JP 09/165532, JP 08/217985, WO 95/20184, JP 07/258580, JP 07/223816, WO 89/12084, EP 624553, JP 08/337422, JP 07/145371, JP 63/308014, JP 07/0256617, EP 359909, FR 1 604 929, DE 19643773, U.S. Pat. No. 5,730,961.

More specifically, the photochromic coloring agents which can be used in the invention are spirooxazines and derivatives thereof, for instance, spiroindolinonaphthoxazines, spironaphthoxazines, naphthopyran and derivatives thereof, spiropyrans, for instance indolinospirobenzopyrans, nitrobenzylpyridines, spirolancs, and titanium or zinc oxides doped with iron. By way of example, specific photochromic agents include those such as the naphthopyran derivatives sold by PPG under the tradenames Photosol 5-68 Photochromic Dye, Photosol 7-49 Photochromic Dye, Photosol 7-106 Photochromic Dye, Photosol 0265 Photochromic Dye and Photosol 0272 Photochromic Dye, these agents having two different colors depending on whether or not they are excited with W. Aluminosilicates doped in particular with S, Se, $SO_4^{2-}$, $W_4^{2-}$ or OH groups or with metal ions, in particular Fe, Cr, Mn, Co or Ni ions, can also be used.

The second component of the composition of the invention can contain one or more agents for screening ultraviolet light. These screening agents include inorganic screening agents, for instance, titanium or zinc oxide powders, in particular of nanometric size, or alternatively organic screening agents. These screening agents can be hydrophilic or lipophilic and can be active in the WA and/or WB range.

The organic screening agents can be chosen in particular from cinnamic derivatives, salicylic derivatives (lipophilic screening agents), camphor derivatives, sulfonic benzimidazole derivatives, triazine derivatives (lipophilic screening agents), benzophenone derivatives, dibenzoylmethane derivatives, β,β-diphenylacrylate derivatives, p-aminobenzoic acid derivatives (hydrophilic screening agents) and lipophilic screening polymers and screening silicones, described in patent application WO 93/04665, and mixtures thereof.

a) Hydrophilic Screening Agents

Suitable hydrophilic screening agents which can be used in the invention include those described in patent application EP 0 678 292. These screening agents comprise at least one carboxylic or sulfonic acid radical.

Examples of screening agents containing an $SO_3H$ group include sulfonic derivatives of 3-benzylidene-2-camphor and in particular those of formulae (I), (II), (III), (IV) and (V) below:

Formula (I):

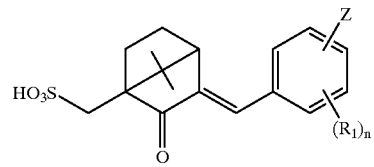

in which:

Z denotes a group,

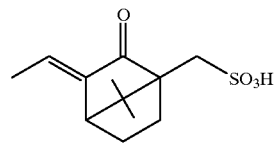

n is equal to 0 or is an integer ranging from 1–4, $R_1$ represents one or more identical or different, linear or branched alkyl or alkoxy radicals containing from 1–carbon atoms.

A preferred compound is benzene-1,4-[bis(3-methylidenecamphor-10-sulphonic acid)] (n=0 in formula I) is used; this screening agent being known under the trade name Mexoryl SX.

Formula (II):

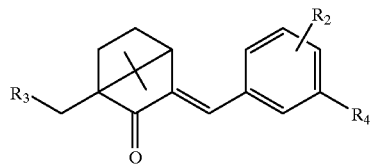

in which:

R₂ denotes a hydrogen or halogen atom, an alkyl radical containing from 1–4 carbon atoms or an —SO₃H radical, R₃ and R₄ denote a hydrogen atom or an —SO₃H radical, at least one of the radicals R₂, R₃ or R₄ denoting an —SO₃H radical, R₂ and R₄ not simultaneously denoting an —SO₃H radical.

Specific examples of compounds of formula (II) include 4-(3-methylidenecamphor)benzenesulfonic acid (R₂=—SO₃H in the para position of the benzylidenecamphor and R₃ and R₄=H); 3-benzylidenecamphor-10-sulfonic acid (R₂ and R₄ =H and R₃=—SO₃H); 2-methyl-5-(3-methylidenecamphor)benzenesulfonic acid (R₂=methyl in the para position of the benzylidenecamphor, R₄=—SO₃H and R₃=H); 2-chloro-5-(3-methylidenecamphor) benzenesulfonic acid (R₂=chlorine in the para position of the benzylidinecamphor, R₄=—SO₃H and R₃=H); 3-(4-methyl)benzylidenecamphor-10-sulfonic acid (R₂=methyl in the para position of the benzylidenecamphor, R₄=H and R₃=—SO₃H)

Formula (III):

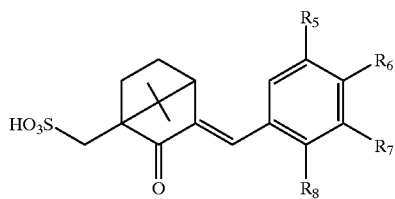

in which:

R₅ and R₇ each is a hydrogen atom, an hydroxyl radical, a linear or branched alkyl or alkoxy radical containing from 1–8 carbon atoms, at least one of the radicals R₅ and R₇ being a hydroxyl, alkyl or alkoxy radical, R₆ and R₈ each is hydrogen atom or a hydroxyl radical, at least one of the radicals R₆ and R₈ being a hydroxyl radical, with the proviso that when each of R₅ and R₈ is a hydrogen atom and when R₆ is a hydroxyl radical, R₇ cannot be an alkoxy radical or a hydrogen atom.

Specific examples of compounds of formula (III) include (3-t-butyl-2-hydroxy-5-methyl)benzylidenecamphor-10-sulfonic acid (R₅=CH₃, R₆=H, R₇=tert-butyl, R₈=—OH); (3-t-butyl-2-hydroxy-5-methoxy)benzylidenecamphor-10-sulfonic acid (R₅=methoxy, R₆=H, R₇=tert-butyl, R₈=hydroxyl); (3,5-di-tert-butyl-4-hydroxy) benzylidenecamphor-10-sulfonic acid (R₅=R₇=tert-butyl, R₆=hydroxyl, R₈=H).

Formula (IV):

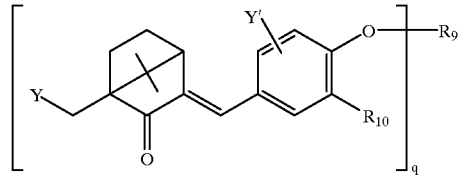

in which:

R₉ is a hydrogen atom, a linear or branched alkyl radical containing from 1–18 carbon atoms, a linear or branched alkenyl radical containing from 3–18 carbon atoms, a group

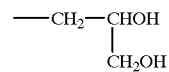

or —(CH₂CH₂O)ₙ—H, or —CH₂—CHOH—CH₃, or a divalent radical: —(CH₂)ₘ— or —CH₂—CHOH—CH₂—, n being an integer ranging from 1–6 and m being an integer ranging from 1–10, R₁₀ denotes a hydrogen atom, an alkoxy radical containing from 1–4 carbon atoms or a divalent radical —O— linked to the radical R₉ when the latter is also divalent, q denotes an integer equal to 1 or 2, it being understood that if q is equal to 1, R₉ must denote a monovalent radical, Y and Y' each is a hydrogen atom or an —SO₃H radical, at least one of these two radicals Y or Y' being other than hydrogen.

Specific examples of compounds of formula (IV) include 2-methoxy-5-(3-methylidenecamphor)benzenesulfonic acid (q=1, Y=R₁₀=H, R₉=methyl, Y' in position 3 =—SO₃H) ; 3-(4,5-methylene-dioxy)benzylidenecamphor-10-sulfonic acid (q=1, Y=—SO₃H, Y'=H, R₁₀=—O— linked to R₉ denoting a methylene radical); 3-(4-methoxy) benzylidenecamphor-10-sulfonic acid (q=1, Y=—SO₃H, Y'=R₁₀=H, R₅=CH₃); 3-(4,5-dimethoxy) benzylidenecamphor-10-sulfonic acid (q=1, Y=—SO₃H, Y'=H, R₉=methyl, R₁₀=methoxy); 3-(4-n-butoxy) benzylidenecamphor-10-sulfonic acid (q=1, Y=—SO₃H, Y'=R₁₀=H and R₉=n-butyl); 3-(4-n-butoxy-5-methoxy) benzylidenecamphor-10-sulfonic acid (q=1, Y=—SO₃H, Y'=H, R₉=n-butyl and R₁₀=methoxy).

Formula (V):

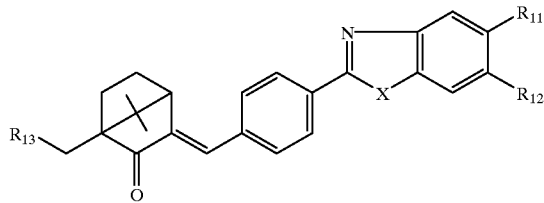

in which:

R₁₁ is a hydrogen atom, a linear or branched alkyl or alkoxy radical containing from 1–6 carbon atoms or an —SO₃H radical, R₁₂ is a hydrogen atom or a linear or branched alkyl or alkoxy radical containing from 1–6 carbon atoms, $R_{13}$ is a hydrogen atom or an —$SO_3H$ radical, at least one of the radicals $R_{11}$ and $R_{13}$ denoting an —$SO_3H$ radical, X is an oxygen or sulfur atom or a group —NR—, R being a hydrogen atom or a linear or branched alkyl radical containing from 1–6 carbon atoms.

A specific example of a compound of formula (V) is 2-[4-(camphormethylidene)phenyl]benzimidazole-5-sulfonic acid in which X=—NH—, $R_{11}$=—$SO_3H$ and $R_{12}$=$R_{13}$=H.

The compounds of formula (I), (II), (III), (IV) and (V) are described, respectively, in documents U.S. Pat. No. 4,585,597, FR 2,236,515, FR 2,282,426, FR 2,645,148, FR 2,430,938 and FR 2,592,380.

The screening agent can also be a sulfonic derivative of benzophenone of formula (VI):

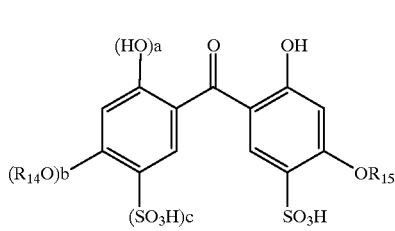

(VI)

in which:
$R_{14}$ and $R_{15}$, which may be identical or different, are each a hydrogen atom or a linear or branched alkyl radical containing from 1–8 carbon atoms, a, b and c, which may be identical or different, are numbers equal to 0 or 1.

A specific example of a compound of formula (VI) is 2-hydroxy-4-methoxybenzophenone-5-sulfonic acid, wherein a, b and c are equal to 0 and $R_{15}$=methyl.

The screening agent can also be a sulfonic derivative of formula (VII):

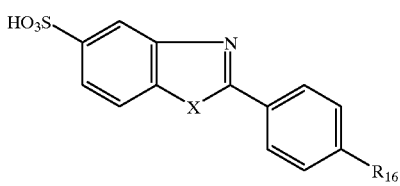

(VII)

in which
X is an oxygen atom or an —NH— radical,
$R_{16}$ is a hydrogen atom, a linear or branched alkyl or alkoxy radical containing from 1–8 carbon atoms or a group of formula (VIII)

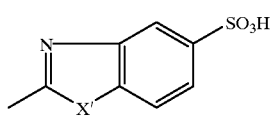

(VIII)

in which X' is an oxygen atom or an —NH— radical.

A specific example of a compound of formula (VII) is 2-phenylbenzimidazole-5-sulfonic acid, in which X=—NH— and $R_{16}$=H. This agent for screening UV-B radiation is sold under the tradename "Eusolex 232" by the company Merck. It is also possible to use benzene-1,4-bis (2-benzimidazolyl-5-sulfonic acid) in which X=—NH—, $R_{16}$ denotes the group of formula (VIII) in which X'=—NH—; benzene-1,4-bis(2-benzoxazolyl-5-sulfonic acid) in which X=H, $R_{16}$ denoting the group of formula (VIII) in which X'=H.

b) Lipophilic Screening Ageists

Lipophilic screening agents which can be used in the invention include dibenzoylmethane derivatives and especially 4-tert-butyl-4'-methoxydibenzoylmethane. These dibenzoylmethane derivatives, which are screening agents that are active in the W-A range, are described in particular in publications FR 2,326,405, FR 2,440,933 and EP 0,114,607; 4-(tert-butyl)-4'-methoxydibenzoylmethane is sold under the tradename "Parsol 1789" by Givaudan. It has the following structural formula:

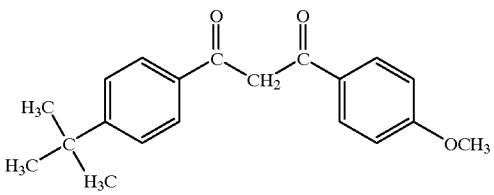

Another dibenzoylmethane derivative which can be used in the invention is 4-isopropyldibenzoylmethane, this screening agent being sold under the tradename "Eusolex 8020" by Merck, which has the following structural formula:

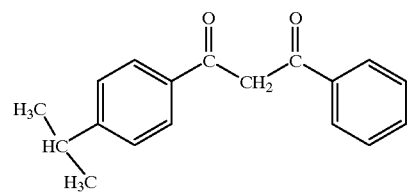

2-Ethylhexyl α-cyano-β,β-diphenylacrylate, also known as octocrylene, can also be used, which is a liquid lipophilic screening agent with activity in the W-B range, commercially available under the tradename "Uvinul N 539" by the company BASF. It has the following formula:

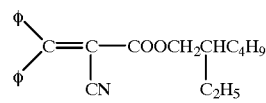

in which Φ denote a phenyl radical.

Another lipophilic screening agent which can be used in the invention is p-methylbenzylidenecamphor, which is known as a UV-B absorbing agent and is sold in particular under the tradename "Eusolex 6300" by Merck.

The titanium or zinc oxide nanopigments which can be used as screening agents in the composition of the invention can be surface-treated or untreated. The titanium oxide can be in rutile, anatase or amorphous form, but is preferably in rutile and/or anatase form.

The term "nanopigments" means pigments whose average elementary particle size ranges from 5–100 nm.

The treated nanopigments can be treated, for example, with alumina, silica, aluminum compounds, silicon compounds, sodium compounds, iron oxides, iron esters, stearic acid or glycerol. More particularly, the treated nanopigments can be titanium oxides treated with silica or alumina, such as the products:

"Microtitanium dioxide MT 500 SA" and "Microtitanium dioxide MT 100 SA" from Tayca, and the products "Tioveil Fin", "Tioveil OP", "Tioveil MOTG" and "Tioveil IPM" from Tioxide, alumina and aluminum stearate, such as the product "Microtitanium dioxide MT 100 T" from Tayca, alumina and aluminum laurate, such as the product "Microtitanium dioxide MT 100 S" from Tayca, iron oxides and iron stearate, such as the product "Microtitanium dioxide MT 100 F" from Tayca, silica, alumina and silicone, such as the products "Microtitanium dioxide MT 100 SAS", "Microtitanium dioxide MT 600 SAS" and "Microtitanium dioxide MT 500 SAS" from Tayca, sodium hexametaphosphate, such as the product "Microtitanium dioxide MT 150 W" from Tayca, octyltrimethoxysilane, such as the product "T-805" from Degussa, alumina and stearic acid, such as the product "UVT-M 160" from Kemira, alumina and glycerol, such as the product "UVT-M212" from Kemira, alumina and silicone, such as the product "W T-M262" from Kemira.

The untreated titanium nanooxides can be, for example, those sold by Tayca under the tradenames "Microtitanium dioxide MT 500 B" and "Microtitanium dioxide MT 600 B".

The screening agent(s) can be present in each component of the composition of the invention at a content ranging from 0.01–30 relative to the total weight of the composition, preferably from 0.5–20%. Depending on the nature and amount of screening agent used, it is possible to obtain total or partial screening of the W rays and to obtain different shades of color intensity.

The second component of the composition can also contain monochromatic coloring agents selected in particular from monochromatic dyes, monochromatic pigments and pearlescent agents conventionally used in cosmetic compositions, and combinations thereof.

The term "pigments" should be understood as referring to white or colored, inorganic or organic particles, which are insoluble in the liquid fatty phase, intended to color and/or opacify the second component. The term "pearlescent agents" should be understood as referring to iridescent particles, in particular particles produced by certain molluscs in their shell, or alternatively synthesized particles. The term "dyes" should be understood as referring to compounds, generally organic compounds, which are soluble in fatty substances, such as oils, or in an aqueous-alcoholic phase.

The coloring agent in each of the first and second coats can be present in an amount of from 0.01–60% relative to the total weight, respectively, of the first component and second component, preferably from 0.05–30% and more particularly from 1–20%, for non-pulverulent compositions. For pulverulent compositions, the amount of coloring agents can be up to 85% and even up to 98%.

Monochromatic inorganic pigments which can be used in the invention include titanium oxide, zirconium oxide or cerium oxide, and zinc oxide, iron oxide or chromium oxide and ferric blue. Suitable organic pigments which can be used in the invention include carbon black, and barium, strontium, calcium and aluminum lakes.

The dyes can be liposoluble or water-soluble. The liposoluble dyes include, for example, Sudan red, DC Red 17, DC Green 6, β-carotene, soybean oil, Sudan brown, DC Yellow 11, DC Violet 2, DC Orange 5 or quinoline yellow. They can be present in an amount ranging from 0.01–20% of the total weight of the second component and better still from 0.1–10%. The water-soluble dyes are, in particular, copper sulfate, iron sulfate, water-soluble sulfopolyesters such as those described in documents FR-96 154,152, rhodamines, natural dyes (carotene, beetroot juice) or methylene blue.

The pearlescent agents can be present in the second component in an amount of from 0–20% relative to the total weight of the said second component, preferably in a content from about 1 to about 15%. Suitable pearlescent agents which can be used in the second component include mica coated with titanium oxide, with iron oxide, with natural pigment or with bismuth oxychloride such as colored titanium mica.

The first and second components of the composition of the invention can moreover comprise any ingredient conventionally used in the fields concerned, and more especially in cosmetics and dermatology. These ingredients are selected in particular from fatty substances, preserving agents, stabilizers, neutralizing agents, aqueous-phase thickeners (polysaccharide biopolymers, synthetic polymers) or fatty-phase thickeners such as clays, fillers, fragrances, hydrophilic or lipophilic active agents. surfactants, antioxidants, film-forming polymers and mixtures thereof. The amounts of these various ingredients are those conventionally used in the fields concerned, ranging, for example, from 0.01–30% relative to the total weight of the composition. The nature of these ingredients and the amounts thereof must be compatible with the production of compositions of the invention, which are stable, thickened and glossy.

The composition can also contain water in an amount ranging from 0–95% relative to the total weight of the composition, or an organic solvent(s) in an amount of up to 90%.

The term "fillers" should be understood as referring to colorless or white, inorganic or synthetic, lamellar or non-lamellar particles. These fillers can be introduced into the first or second coats in order, in particular, to modify the texture of these compositions. They can be present in an amount of from 0–35% relative to the total weight of each composition, preferably 0.5–15%. Suitable examples of fillers include talc, zinc stearate, mica, kaolin, Nylon powders (in particular Orgasol), polyethylene powder, Teflon, starch, boron nitride, copolymer microspheres such as Expancel (Nobel Industrie), Polytrap (Dow Corning) and silicone resin microbeads (Tospearl from Toshiba, for example), silica and the like.

The first and second components of the present composition advantageously comprise a fatty phase containing fatty substances which are liquid, solid or pasty at room temperature. The fatty substances which are solid at room temperature allow the composition to be structured; they are selected from gums and/or waxes. The waxes can be hydrocarbon-based, fluorine-based and/or silicone-based and can be of plant, mineral, animal and/or synthetic origin. In particular, the waxes have a melting point above 25° C. and better still above 45° C.

Suitable waxes which can be used in the first and second components of the invention, include lanolin, beeswax, carnauba wax or candelilla wax, paraffin, lignite wax, microciystalline wax, ceresin or ozokerite; synthetic waxes such as polyethylene waxes, Fischer-Tropsch waxes, silicone waxes such as alkyl- or alkoxydimethicone containing from 16–45 carbon atoms.

The gums are, in particular, organopolysiloxanes such as PDMS with an average molecular weight of from 1,000–500,000.

The nature and amount of these gums or waxes depend on the desired mechanical and textural properties. As a guide, each composition can contain from 0–50% by weight of waxes relative to the total weight of the composition, and better still from 5–30%, and from 0–20% of gum.

Suitable fatty substances which are liquid at room temperature, which can be used in the compositions of the invention, include hydrocarbon-based oils of animal origin such as perhydrosqualene; hydrocarbon-based plant oils such as liquid triglycerides of fatty acids of 4–10 carbon atoms such as triglycerides of heptanoic and octanoic acids, or alternatively sunflower oil, corn oil, soybean oil, marrow oil, grapeseed oil, sesame oil, hazelnut oil, apricot oil, macadamia oil, castor oil, avocado oil, caprylic/capric acid triglycerides such as those sold by Stearineries Dubois or those sold under the tradenames Miglyol 810, 812 and 818 by Dynamit Nobel, jojoba oil or karite butter;

linear or branched hydrocarbons of mineral or synthetic origin such as liquid paraffins and derivatives thereof, petroleum jelly, polydecenes, hydrogenated polyisobutene such as parleam; isoparaffins such as isohexadecane and isodecane;

synthetic esters and ethers, in particular those of fatty acids such as the oils of fomula $R_1COOR_2$ in which $R_1$ is a higher fatty acid residue comprising from 7–29 carbon atoms and $R_2$ is a hydrocarbon-based chain containing from 3–30 carbon atoms such as, for example, purcellin oil, isopropyl myristate, 2-ethylhexyl palmitate, 2-octyldodecyl stearate, 2-octyldodecyl erucate, isostearyl isostearate; hydroxylated esters such as isostearyl lactate, octyl hydroxystearate, octyldodecyl hydroxystearate, diisostearyl malate, triisocetyl citrate, heptanoates, octanoates and decanoates of fatty alcohols; polyol esters such as propylene glycol dioctanoate, neopentyl glycol diheptanoate, diethylene glycol diisononanoate; and pentaerythritol esters;

fatty alcohols containing from 12–26 carbon atoms such as octyldodecanol, 2-butyloctanol, 2-hexyldecanol, 2-undecylpentadecanol and oleyl alcohol;

partially hydrocarbon-based and/or silicone-based fluoro oils such as those described in document JP 2,295,912;

silicone oils such as volatile or non-volatile, linear or cyclic polymethylsiloxanes (PDMS) which are liquid or pasty at room temperature; phenylsilicones such as phenyltrimethicones, diphenyldimethicones, phenyldimethicones and phenyltrimethylsiloxydiphenyl siloxanes;

fluoro oils and fluorosilicone oils;

mixtures thereof.

These oils range in amount from 0–99.9% relative to the total weight of each component of the composition.

Suitable volatile silicone oils which can be used in the invention include linear or cyclic silicones containing from 2–7 silicon atoms, these silicones optionally comprising alkyl groups containing from 1–10 carbon atoms. Thus, these silicones are, in particular, hexamethyldisiloxane, cyclopenta- or cyclotetra- or cyclohexadimethylsiloxane. These volatile oils range in amount from 0–50% relative to the total weight of the composition.

Suitable solvents for use in the invention include:

ketones, which are liquid at room temperature, such as methyl ethyl ketone, methyl isobutyl ketone, diusobutyl ketone, isophorone, cyclohexanone and acetone;

alcohols, which are liquid at room temperature, such as ethanol, isopropanol, diacetone alcohol, 2-butoxycthanol and cyclohexanol;

glycols, which are liquid at room temperature, such as ethylene glycol, propylene glycol and pentylene glycol;

propylene glycol ethers, which are liquid at room temperature, such as propylene glycol monomethyl ether, propylene glycol monomethyl ether acetate and dipropylene glycol mono-n-butyl ether;

short-chain esters, containing from 3–8 carbon atoms in total, such as ethyl acetate, methyl acetate, propyl acetate, n-butyl acetate and isopentyl acetate;

ethers, which are liquid at room temperature, such as dicthyl ether, dimethyl ether and dichlorodiethyl ether;

alkanes, which are liquid at room temperature, such as decane, heptane, dodecane and cyclohexane;

aromatic cyclic compounds, which are liquid at room temperature, such as toluene and xylene;

aldehydes which are liquid at room temperature, such as benzaldehyde and acetaldehyde.

These solvents are more particularly suitable for making-up and caring for the nails: in this case, the composition constitutes a nail varnish or a nailcare product. Water and aqueous-alcoholic media can also be used as solvents.

Suitable film-forming polymers, which can be used in the invention, include nitrocellulose, cellulose acetobutyrate, polyvinyl butyrals, alkyd resins, resins resulting from the condensation of formaldehyde with an arylsulfonamide, polyesters, polyurethanes, polyesterpolyurethanes, polyetherpolyurethanes, radical polymers, in particular of the acrylic, styrene acrylic and/or vinyl type, and mixtures thereof.

The polymers can be dissolved or dispersed in the composition. They can be present in a content ranging from 0–40% by weight relative to the total weight of the composition, for example from 0.5–40% and better still ranging from 10–20% by weight.

The composition according to the invention can also comprise, in addition to the film-forming polymer(s), plasticizers which allow the flexibility of the film of polymer to be adjusted without weakening its physical strength.

The plasticizers which can be used are those commonly used in nail varnish compositions. Suitable plasticizers include dibutyl, dioctyl, dilsobutyl and dimethoxyethyl phthalate, benzyl and glyceryl benzoate; tricthyl and tributyl citrate and tributyl acetyl citrate; tributyl and triphenyl phosphate; glycols, camphor as well as derivatives thereof, and mixtures thereof. The plasticizers can generally be present in a content ranging from 0–30% relative to the total weight of the composition, for example from 1–30% and better still from 5–10%.

The compositions of the invention can be in any pharmaceutical form normally used for topical application, and in particular in the form of an oily or aqueous solution, an oily or aqueous gel, an oil-in-water or water-in-oil emulsion, a dispersion of oil in water by means of vesicles, the vesicles being at the oil/water interface, or alternatively a powder. Each composition can have the appearance of a lotion, a cream, a salve, a soft paste, an ointment, a cast or molded solid and in particular as a stick or a dish, or alternatively a compacted solid.

The product according to the invention can advantageously be used for making-up the skin and/or mucous membranes and/or superficial body growths, depending on the nature of the ingredients used. In particular, each composition of the invention can be in the form of a lipstick tube or paste, a solid foundation, a concealer product or a product for the area around the eyes, an eyeliner, a mascara, an eyeshadow, a solvent-based or water-based nail varnish, a body make-up product or a skin coloring product. These compositions can also contain cosmetic or dermatological active agents, in order, in particular, to give the composition a care or treating aspect. Thus, these compositions can contain vitamins and other lipophilic active agents (lanolin) or hydrophilic active agents which include moisturizers such as glycerol.

An aspect of the invention is also a lipstick, a foundation, a tattoo, a nail varnish, a face powder or an eyeshadow containing a cosmetically acceptable medium and first and second compositions as described above.

The compositions of the invention can be obtained by heating the various constituents to the melting point of the waxes which is the highest, followed by casting the molten mixture in a mold (dish or glove-finger). They can also be obtained by extrusion as described in patent application EP-A-667,146.

Having now generally described the invention, a further understanding can be obtained by reference to certain specific examples which are provided herein for purpose of illustration only and are not intended to be limiting unless otherwise specified. The amounts herein are given in percent by weight.

Preparation Example:
Nail varnish

| a) The nail varnish (referred to as VAO base) used for the two coats of a composition is as follows: | |
|---|---|
| Modified hectorite | 1.4% |
| Nitrocellulose (30 in isopropopyl alcohol) | 14.5% |
| Alkyd resin (30% in ethyl acetate) | 16.5% |
| Tributyl acetyl citrate | 7.0% |
| Isopropyl alcohol | 3.7% |
| Ethyl acetate | 22.8% |
| Butyl acetate qs | qs 100% |
| b) The component which forms the nail varnish basecoat is constituted of: | |
| VAO base | 98.0% |
| Photosol 5-3 Photochromic Dye from PPG | 2.0% |

This composition is obtained by mixing the VAO base and the photochromic pigment at room temperature, with stirring. Its color changes, depending on the presence or absence of W rays, range from colorless to yellow. This composition is applied continuously, in the form of a single coat, to nails from which make-up has been removed.

| c) The component of a composition for forming the nail varnish top coat contains: | |
|---|---|
| VAO base | 95.0% |
| Nanometric titanium dioxide (MT 100T) | 5.0% |

The composition of the top coat is transparent. It is obtained by mixing the pigments and the VAO base as performed conventionally for the manufacture of a varnish.

This surface composition is applied with a fine brush to the basecoat, forming a pattern such as marks, stars or butterflies. After drying the double-coat, this coat allows the nail to be seen in the absence of W rays (in a residence, in particular). On the other hand, in the presence of UV rays (in daylight, in particular), the basecoat turns yellow and thus reveals patterns of the color of the nail on a yellow background. When the exposure to UV rays is eliminated, the pattern disappears.

The disclosure of French priority Application Number 9808085 filed Jun. 25, 1998 is hereby incorporated by reference into the present application.

Obviously, numerous modifications and variations of the present invention are possible in light of the above teachings. It is, therefore, to be understood that within the scope of the appended claims, the invention may be practiced otherwise than as specifically described herein.

What is claimed as new and is intended to be secured by Letters Patent is:

1. A cosmetic make-up product, comprising first and second components, separately packaged, each containing a cosmetically acceptable medium, the first component containing at least one photochromic coloring agent which is capable of producing at least one color in the presence of ultraviolet light, and the second component containing at least one agent which screens ultraviolet light.

2. The product according to claim 1, wherein the photochromic coloring agent is selected from the group consisting of spirooxazincs and derivatives thereof, spironaphthoxazincs, naphthopyran and derivatives thereof, spiropyrans, nitrobenzylpyridines, spirolancs, titanium or zinc oxides doped with iron, aluminosilicates doped with metal ions or is a group selected from the group consisting of Se, S, OH, $SO_4^{2-}$ and $WO_4^{2-}$.

3. The product according to claim 1, wherein the screening agent is selected from the group consisting of treated or untreated titanium or zinc nanooxides, cinnamic derivatives, salicylic derivatives, camphor derivatives, sulfonic benzimidazole derivatives, triazine derivatives, benzophenone derivatives, dibenzoylmethane derivatives, $\beta,\beta$-diphenylacrylate derivatives, p-aminobenzoic acid derivatives, lipophilic screening polymers and screening silicones, and mixtures thereof.

4. The product according to claim 1, wherein the screening agent ranges from 0.01–30% of the total weight of the second component.

5. The product according to claim 1, wherein the second component contains at least one monochromatic coloring agent.

6. The product according to claim 1, wherein the monochromatic coloring agent is selected from the group consisting of monochromatic dyes, monochromatic pigments, pearlescent agents and combinations thereof.

7. The product according to claim 5, wherein the monochromatic coloring agent is selected from the group consisting of titanium oxide, zirconium oxide, cerium oxide, zinc oxide, iron oxide, chromium oxide, ferric blue, carbon black, barium, strontium, calcium or aluminum lakes, Sudan red, DC Red 17, DC Green 6, $\beta$-carotene, soybean oil, Sudan Brown, DC Yellow 11, DC Violet 2, DC Orange 5, Quinoline Yellow and mica coated with titanium oxide, with iron oxide, with natural pigment or with bismuth oxychloride.

8. The product according to claim 1, wherein each coloring agent ranges from 0.01–98% relative to the total weight of the product.

9. The product according to claim 1, which is packaged in the form of a foundation, a nail varnish or a make-up product for the body or the lips, face powder or an eye shadow.

10. The product according to claim 1, wherein each component is in the form of an oily or aqueous solution, an oily or aqueous gel, an oil-in-water or water-in-oil emulsion, a dispersion of oil in water by means of vesicles, the vesicles being at the oil/water interface, or a powder.

11. The product according to claim 1, wherein the cosmetically acceptable medium also contains at least one ingredient selected from the group consisting of oils, solvents, waxes, film forming polymers, fillers, hydrophilic or lipophilic active agents, aqueous-phase thickeners or fatty-phase thickeners, Surifactants, antioxidants, fragrances, plasticizers, neutralizing agents, stabilizers and preserving agents.

12. A method of making-up the human skin, lips and/or superficial body growths, which comprises:

applying a first coat of a first component comprising a cosmetically acceptable medium and at least one photochromic coloring agent to the skin, the lips and/or superficial body growths, and then applying a second coat of a second component comprising a cosmetically acceptable medium and at least one agent which screens ultraviolet light over a part of the said first coat.

13. The method according to claim 12, wherein the second coat is discontinuous.

14. The method according to claim 12, wherein the second coat comprises patterns.

15. The method according to claim 12, wherein the second coat contains patterns distributed in a random or ordered manner, of symmetrical or asymmetrical shape.

16. The method according to claim 12, wherein the photochromic coloring agent is selected from the group consisting of spirooxazines and derivatives thereof, spironaphthoxazines, naphthopyran and derivatives thereof, spiropyrans, nitrobenzylpyridines, spirolanes, titanium or zinc oxides doped with iron and aluminosilicates doped with metal ions or is selected from the group consisting of Se, S. OH, $SO_4^{-2}$ and $WO_4^{-2}$.

17. The method according to claim 12, wherein the second component contains at least one additional monochromatic coloring agent.

18. The method according to claim 12, wherein the monochromatic coloring agent is selected from the group consisting of monochromatic dyes, monochromatic pigments, pearlescent agents and combinations.

19. The method according to claim 17, wherein the monochromatic coloring agent is selected from the group consisting of titanium oxide, zirconium oxide, cerium oxide, zinc oxide, iron oxide, chromium oxide, ferric blue, carbon black, barium, strontium, calcium or aluminum lakes, Sudan red, DC Red 17, DC Green 6, β-carotene, soybean oil, Sudan Brown, DC Yellow 11, DC Violet 2, DC Orange 5, Quinoline Yellow and mica coated with titanium oxide, with iron oxide, with natural pigment or with bismuth oxychloride.

20. A make-up kit comprising the product according to claim 1.

21. The kit according to claim 20, which contains means for applying the first and second components to the skin and/or mucous membranes and/or superficial body growths.

22. The kit according to claim 21, which means are selected from the group consisting of fine brushes, pens, brushes, feathers and pencils.

23. The kit according to claim 20, wherein the first and second components are packaged in separate compartments or containers.

24. A method of making patterns of color appear or disappear on human skin and/or lips and/or superficial body growths, comprising:

applying the first and second components of the composition of claim 1 to said body areas, the development of color depending upon the exposure or absence of exposure to ultraviolet light.

25. A made-up support, comprising:

a first coat of a first component comprising at least one photochromic coloring agent and a second coat of a second component partly applied onto the first coat and comprising at least one agent to screen ultraviolet light.

26. The support according to claim 25, which is in the form of false nails, false eyelashes or wigs.

27. The support according to claim 25, wherein the second coat is discontinuous.

28. The support according to claim 25, wherein the second coat comprises patterns distributed in a random or ordered manner.

29. The support according to claim 25, wherein the photochromic coloring agent is selected from the group consisting of spirooxazines and derivatives thereof, spironaphthoxazines, naphthopyran and derivatives thereof, spiropyrans, nitrobenzylpyridincs, spirolanes, titanium and zinc oxides doped with iron or aluminosilicates doped with metal ions or is a group selected from the group consisting of Se, S, OH, $SO_4^{2-}$ and $WO_4^{2-}$.

30. The support according to claim 25, wherein the screening agent is selected from the group consisting of treated or untreated titanium or zinc nanooxides, cinnamic derivatives, salicylic derivatives, camphor derivatives, sulfonic benzimidazole derivatives, triazine derivatives, benzophenone derivatives, dibenzoylmethane derivatives, β,β-diphenylacrylate derivatives, p-aminobenzoic acid derivatives, lipophilic screening polymers and screening silicones, and mixtures thereof.

31. The support according to claim 25, wherein the second component contains at least one monochromatic coloring agent.

* * * * *